(12) United States Patent
Ono (10) Patent No.: US 11,580,875 B2
(45) Date of Patent: Feb. 14, 2023

(54) CLEANUP SUPPORT SYSTEM, CLEANUP SUPPORT METHOD, AND RECORDING MEDIUM

(71) Applicant: PANASONIC INTELLECTUAL PROPERTY MANAGEMENT CO., LTD., Osaka (JP)

(72) Inventor: Marina Ono, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 301 days.

(21) Appl. No.: 16/761,197

(22) PCT Filed: Oct. 23, 2018

(86) PCT No.: PCT/JP2018/039277
§ 371 (c)(1),
(2) Date: May 1, 2020

(87) PCT Pub. No.: WO2019/087854
PCT Pub. Date: May 9, 2019

(65) Prior Publication Data
US 2020/0342780 A1    Oct. 29, 2020

(30) Foreign Application Priority Data

Nov. 6, 2017  (JP) .............................. JP2017-213820
Nov. 6, 2017  (JP) .............................. JP2017-213957

(51) Int. Cl.
*G09B 19/00*        (2006.01)
*G05B 19/4155*      (2006.01)
(Continued)

(52) U.S. Cl.
CPC ......... *G09B 19/00* (2013.01); *G05B 19/4155* (2013.01); *G06N 7/005* (2013.01);
(Continued)

(58) Field of Classification Search
None
See application file for complete search history.

(56) References Cited

U.S. PATENT DOCUMENTS 5,621,429 A      4/1997  Yamaashi et al.
7,522,057 B2 *   4/2009  Stern .................. G08B 21/0476
                                                 340/568.1
(Continued)

FOREIGN PATENT DOCUMENTS

JP    H06-324662 A    11/1994
JP    2004-078304 A    3/2004
(Continued)

OTHER PUBLICATIONS

Seright "Cleanup of Oil Zones After a Gel Treatment R.S", 2006, SPE, New Mexico Petroleum Recovery Research C, pp. 237-244 (Year: 2006).*

(Continued)

*Primary Examiner* — Romain Jeanty
(74) *Attorney, Agent, or Firm* — McDermott Will & Emery LLP (57) ABSTRACT

A cleanup support system that supports a cleanup behavior includes: a first obtaining unit configured to obtain first information indicating a level of interest of a target person in cleanup; a second obtaining unit configured to obtain second information indicating a level of achievement of the cleanup performed by the target person; a determination unit configured to determine a content of control corresponding to the first information obtained and the second information obtained, with reference to a rule which associates the level of interest in the cleanup and the level of achievement of the cleanup with a content of control performed on a device; and a control unit configured to control the device according to the content of control determined.

14 Claims, 5 Drawing Sheets

(51) Int. Cl.
*G06N 7/00* (2023.01)
*G16H 20/70* (2018.01)
*G09B 5/06* (2006.01)
*G06V 40/20* (2022.01)

(52) U.S. Cl.
CPC .... *G05B 2219/32334* (2013.01); *G06V 40/20* (2022.01); *G09B 5/065* (2013.01); *G16H 20/70* (2018.01)

(56) References Cited

U.S. PATENT DOCUMENTS

| | | | | |
|---|---|---|---|---|
| 2008/0248815 | A1* | 10/2008 | Busch | G06Q 20/3224 455/456.5 |
| 2009/0319459 | A1* | 12/2009 | Breazeal | G06N 3/004 901/1 |
| 2010/0185714 | A1* | 7/2010 | Gerber | G06F 16/27 709/227 |
| 2011/0160928 | A1 | 6/2011 | Chen et al. | |
| 2012/0317066 | A1 | 12/2012 | Miyazaki | |

FOREIGN PATENT DOCUMENTS

| | | | |
|---|---|---|---|
| JP | 2004-096501 A | 3/2004 | |
| JP | 2006-178644 A | 7/2006 | |
| JP | 2007-082488 A | 4/2007 | |
| JP | 2008-217478 A | 9/2008 | |
| JP | 2011-138736 A | 7/2011 | |
| JP | 2013-242434 A | 12/2013 | |
| WO | WO-03056457 A2 * | 7/2003 | ........... G06F 16/735 |
| WO | 2011/114620 A1 | 9/2011 | |

OTHER PUBLICATIONS

Alain et al. "Field Evaluation of a Wireless Electronic Shoreline Cleanup Support System", Mar. 1999, International Oil Spill Conference Proceedings, vol. 1999, pp. 859-861; https://doi.org/10.7901/2169-3358-1999-1-859 (Year: 1999).*

International Search Report and Written Opinion dated Jan. 8, 2019 in International (PCT) Application No. PCT/JP2018/039277; with partial English translation.

* cited by examiner

| | | |
|---|---|---|
| RULE FOR QUIET CHILD | CLEANUP BEHAVIOR HAS BEEN ACHIEVED | (1) PRESENT PRAISE VIDEO |
| | CLEANUP BEHAVIOR HAS NOT BEEN ACHIEVED LEVEL OF INTEREST IS LOW (MOVEMENT IS LESS THAN OR EQUAL TO FIXED VALUE) | (2) PLAY CLEANUP-PROMPTING MUSIC |
| | CLEANUP BEHAVIOR HAS NOT BEEN ACHIEVED LEVEL OF INTEREST IS HIGH (MOVEMENT IS MORE THAN OR EQUAL TO FIXED VALUE) | (3) DO NOTHING |
| | CLEANUP BEHAVIOR HAS NOT BEEN ACHIEVED AFTER (2) AND (3) | (4) NOTIFY TABLET |
| RULE FOR ACTIVE CHILD | CLEANUP BEHAVIOR HAS BEEN ACHIEVED | (1) PLAY PRAISE MUSIC |
| | CLEANUP BEHAVIOR HAS NOT BEEN ACHIEVED LEVEL OF INTEREST IS LOW (THERE IS NO MOVEMENT) | (2) PRESENT CLEANUP-PROMPTING VIDEO |
| | CLEANUP BEHAVIOR HAS NOT BEEN ACHIEVED LEVEL OF INTEREST IS HIGH (THERE IS NO MOVEMENT) | (3) DO NOTHING |
| | CLEANUP BEHAVIOR HAS NOT BEEN ACHIEVED AFTER (2) AND (3) | (4) NOTIFY TABLET |
| ⋮ | ⋮ | ⋮ |

CLEANUP SUPPORT SYSTEM, CLEANUP SUPPORT METHOD, AND RECORDING MEDIUM

CROSS-REFERENCE OF RELATED APPLICATIONS

This application is the U.S. National Phase under 35 U.S.C. § 371 of International Patent Application No. PCT/JP2018/039277, filed on Oct. 23, 2018, which in turn claims the benefit of Japanese Application No. 2017-213820, filed on Nov. 6, 2017 and Japanese Application No. 2017-213957, filed on Nov. 6, 2017, the entire disclosures of which Applications are incorporated by reference herein.

TECHNICAL FIELD

The present disclosure relates to a cleanup support system which supports a cleanup behavior, and a cleanup support method and a recording medium for use in the cleanup support system.

BACKGROUND ART

Conventionally known is a technology of controlling a device in order to cause an infant or a dog to learn a specific behavior. For example, Patent Literature (PTL) 1 discloses a technology by which the behavior of entrance into a monitor region by an infant is monitored based on image data recorded with a camera and control of lifting a fence is performed according to the aforementioned behavior or discipline information is outputted. Moreover, Patent Literature (PTL) 2 discloses a technology by which feeding is performed by controlling a feeder unless dog barking is not sensed for fixed time in order to perform efficient dog discipline.

CITATION LIST

Patent Literature

PTL 1: Japanese Unexamined Patent Application Publication No. 2004-78304
PTL 2: Japanese Unexamined Patent Application Publication No. 2007-82488

SUMMARY OF THE INVENTION

Technical Problem

The present invention is focused on a cleanup behavior for a target person such as an infant, and it is an object of the present invention to provide, for example, a cleanup support system capable of increasing the possibility that the target person more spontaneously performs a cleanup behavior than in a conventional case.

Solutions to Problem

To address the object described above, a cleanup support system according to one aspect of the present invention refers to a cleanup support system that supports a cleanup behavior, and includes: a first obtaining unit configured to obtain first information indicating a level of interest of a target person in cleanup; a second obtaining unit configured to obtain second information indicating a level of achievement of the cleanup performed by the target person; a determination unit configured to determine a content of control corresponding to the first information obtained and the second information obtained with reference to a rule which associates the level of interest in the cleanup and the level of achievement of the cleanup with a content of control performed on a device; and a control unit configured to control the device according to the content of control determined.

To address the object described above, a cleanup support method according to another one aspect of the present invention refers to a cleanup support method for supporting a cleanup behavior, and includes: obtaining first information indicating a level of interest of a target person in cleanup; obtaining second information indicating a level of achievement of the cleanup performed by the target person; determining a content of control corresponding to the first information obtained and the second information obtained, with reference to a rule which associates the level of interest in the cleanup and the level of achievement of the cleanup with a content of control performed on a device; and controlling the device according to the content of control determined.

To address the object described above, recording medium according to another one aspect of the present invention, etc., refers to a computer-readable, non-transitory recording medium having recorded thereon a program that causes a computer to execute the cleanup support method described above.

Advantageous Effect of Invention

With the cleanup support system, etc. according to one aspect of the present invention, the possibility that the target person more spontaneously performs a cleanup behavior increases.

DESCRIPTION OF EXEMPLARY EMBODIMENTS

Embodiment

Hereinafter, the embodiments will be described with reference to the drawings. The embodiments described below each illustrate a detailed example. Therefore, numerical values, shapes, components, and arrangement positions and connection modes of the components as well as steps (processes), a sequence of the steps, etc., illustrated in the embodiments below form one example and are not intended to limit the present invention in any manner. Of the components in the embodiments described below, those not described in an independent claim are optional components.

Embodiment

Hereinafter, the embodiment will be described with reference to FIGS. 1 to 5.

[Configuration]

Figure 1:
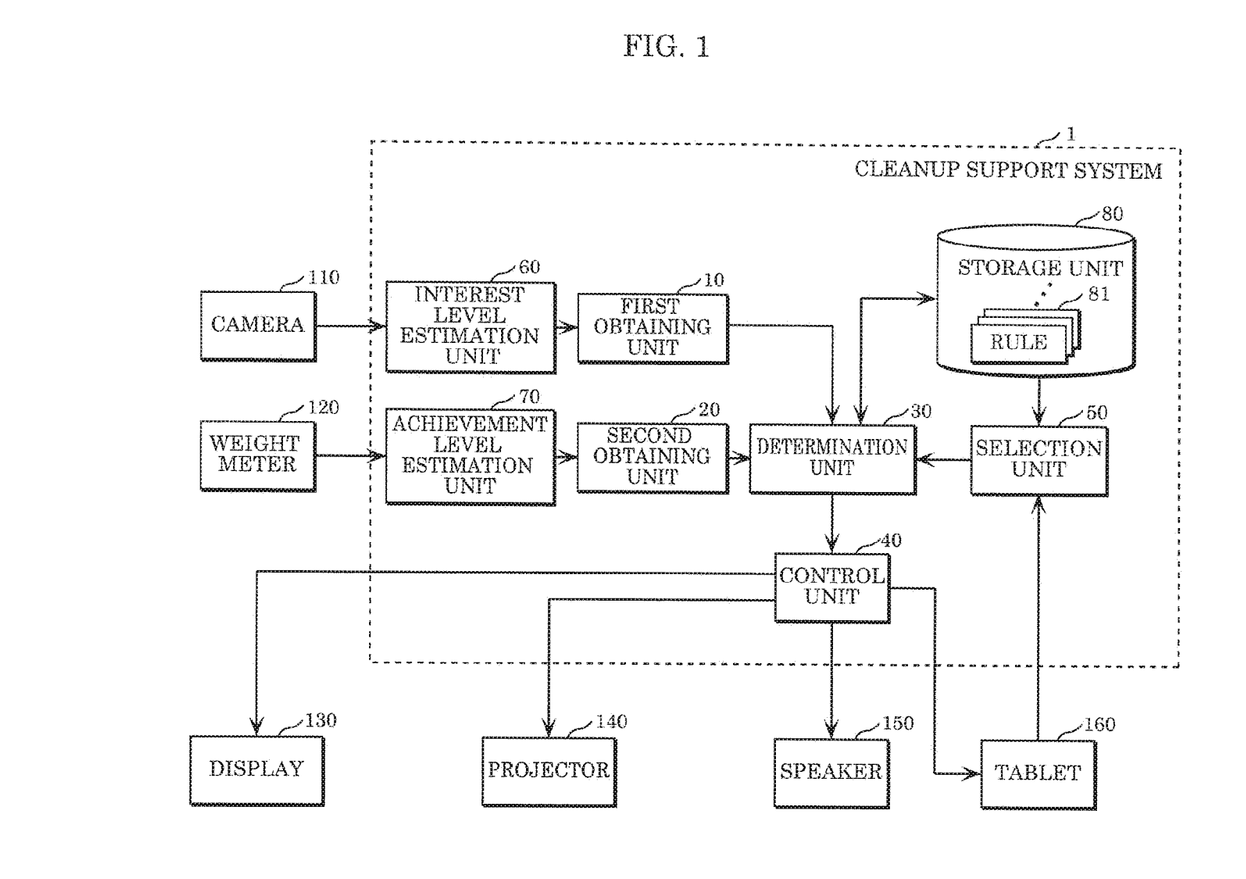
FIG. 1 is a schematic configuration diagram of a cleanup support system according to an embodiment.

FIG. 1 is a schematic configuration diagram of cleanup support system 1 according to the embodiment. Note that FIG. 1 illustrates, in addition to cleanup support system 1, camera 110, weight meter 120, display 130, projector 140, speaker 150, and tablet 160.

Camera 110 is a camera (image sensor) which is capable of communicating with cleanup support system 1 and has the function of photographing, as an object, a predetermined space, for example, a room where a target person such as an infant or a child in a house plays to thereby generate image data related to the aforementioned predetermined space and transmit the image data to cleanup support system 1.

Weight meter 120 is, for example, a scale which is capable of communicating with cleanup support system 1 and has the function of transmitting, to cleanup support system 1, the weight of a toy box installed in the aforementioned predetermined space.

Display 130 is a presentation device which is capable of communicating with cleanup support system 1 and presents contents (for example, moving images) according to control signals provided from cleanup support system 1. For example, display 130 is installed in the aforementioned predetermined space, and presents a video for praising the target person and presents a video for prompting the target person to perform cleanup.

Projector 140 is a presentation device which is capable of communication with cleanup support system 1 and projects the contents (for example, the moving images) on the floor or wall of the aforementioned predetermined space according to the control signals provided from cleanup support system 1. For example, projector 140 is installed in the aforementioned predetermined space and projects, as a moving image prompting the target person to perform the cleanup, such a moving image in which an image indicating a toy moves towards the toy box.

Speaker 150 is an audio playback device which is capable of communicating with cleanup support system 1 and plays back voice according to the control signals provided from cleanup support system 1. For example, speaker 150 is installed in the aforementioned predetermined space and plays back voice for praising the target person and plays back music for prompting the target person to perform the cleanup.

Tablet 160 is a terminal (operation unit) which is held by a caregiver (a parent or the like) of the target person and which is capable of communicating with cleanup support system 1, and displays contents (for example, characters) on a display included in tablet 160 according to the control signals provided from cleanup support system 1. Moreover, tablet 160 displays a plurality of rules on the display and according to operation performed on tablet 160 by the caregiver, transmits, to cleanup support system 1, a fact that one rule from among the plurality of rules has been selected.

Camera 110, weight meter 120, display 130, projector 140, speaker 150, and tablet 160 are devices which are mainly installed in a house or used in the house.

Cleanup support system 1 is one example of a system which supports a cleanup behavior in order to cause a target person such as an infant to learn the behavior of cleaning up a toy or the like (cleanup behavior). Cleanup support system 1 is applied to, for example, home as illustrated in FIG. 2.

Figure 2:
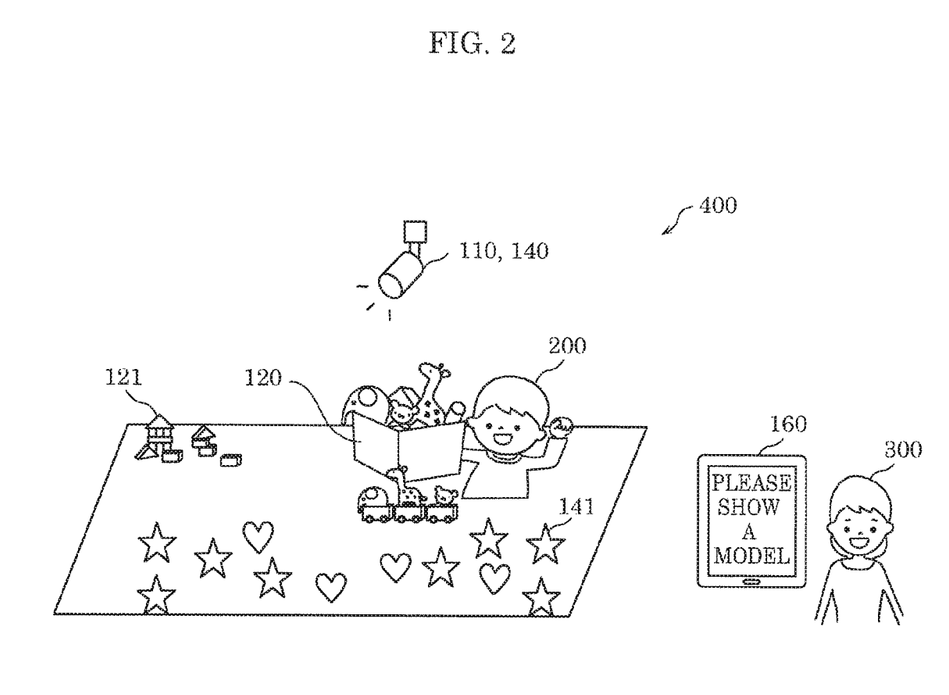
FIG. 2 is a diagram illustrating an application example of the cleanup support system according to the embodiment.

FIG. 2 is a diagram illustrating an application example of cleanup support system 1 according to the embodiment.

FIG. 2 illustrates: a state of space 400, as the aforementioned predetermined space, where infant 200 plays with toy 121; and caregiver 300 located at a place different from a place where space 400 is located.

Camera 110 is set on, for example, the ceiling of space 400 and photographs, as an object, a region (for example, entire space 400) where infant 200 plays. The toy box storing toy 121 is installed in space 400, and weight meter 120 is provided at a bottom of or below the toy box. Projector 140 is set, for example, on the ceiling of space 400 and is integrated with camera 110 in the present example, although projector 140 may be provided separately from camera 110. Projector 140 projects image 141, for example, on the floor of space 400. Moreover, tablet 160 provides such a display, as illustrated in FIG. 2, that prompts infant 200 by caregiver 300 to perform the cleanup according to the control signal provided from cleanup support system 1 in a specific case details of which will be described later on. FIG. 2 does not illustrate display 130 and speaker 150, for example, which are also installed in space 400. Cleanup support system 1 is applicable in such an environment.

The description will be provided below, illustrating, as one example of the cleanup, organization and storage of toys or the like into a toy box or the like, as illustrated in FIG. 2. The caregiver can utilize cleanup support system 1 in order to cause the infant or the like to appropriately learn an organization and storage behavior after playing with the toy. That is, cleanup support system 1 is a system which supports the infant or the like to achieve the cleanup behavior.

As illustrated in FIG. 1, cleanup support system 1 includes first obtaining unit 10, second obtaining unit 20, determination unit 30, control unit 40, selection unit 50, interest level estimation unit 60, achievement level estimation unit 70, and storage unit 80. Note that cleanup support system 1 may include any of camera 110, weight meter 120, display 130, projector 140, speaker 150, and tablet 160.

Cleanup support system 1 is a computer including a processor (microprocessor), a memory (storage unit 80), a communication interface (communication circuit or the like), etc. Hereinafter, communication between cleanup support system 1 and the sensors (camera 110, weight meter 120, etc.) and communication between cleanup support system 1 and the devices (display 130, projector 140, speaker 150, tablet 160, etc.) are performed via the communication interface, description of which is omitted here. Cleanup support system 1 can be realized by a personal computer (PC) or a portable terminal such as a smartphone or a tablet. Note that cleanup support system 1 may be realized by a server usable via a network such as the Internet, i.e., a so-called cloud server. The memory (storage unit 80) is a ROM, a RAM, or the like and can store control programs (computer programs) executed by the processor. For example, the processor operates according to the control programs (computer programs) whereby cleanup support system 1 realizes first obtaining unit 10, second obtaining unit 20, determination unit 30, control unit 40, selection unit 50, interest level estimation unit 60, and achievement level estimation unit 70.

Cleanup support system 1 is realized by, for example, one portable terminal, one cloud server, or the like, but may be realized by a plurality of portable terminals or a plurality of servers, in which case each of the functional components may be arranged in the plurality of portable terminals or the plurality of servers in a dispersed manner. Specifically, as one example, first obtaining unit 10, second obtaining unit 20, determination unit 30, control unit 40, selection unit 50, interest level estimation unit 60, and achievement level estimation unit 70 may be arranged in one of the plurality of servers and storage unit 80 may be arranged in another one of the plurality of servers. The way of dispersing the functional components is not limited to the aforementioned way and not specifically limited.

Interest level estimation unit 60 has the function of obtaining, from camera 110, the image (image data) sequentially generated by photographing upon the performance of the behavior by the target person and estimating the level of interest of the target person in the cleanup based on the aforementioned image. For example, interest level estimation unit 60 judges, based on the image sequentially generated by photographing, whether or not there is any movement of the target person, whether or not the movement is large, whether or not face orientation does not change for fixed time, etc. The aforementioned judgments are performed based on, for example, image recognition or mechanical learning. Moreover, storage unit 80 stores association between the level of interest of the target person in the cleanup and a content of a behavior to be performed by the target person. For example, the aforementioned association includes: association between the high level of interest and the content of behavior such that the face orientation of the target person is directed towards the toy box; and association between the low level of interest and the content of the behavior such that the face orientation of the target person is not directed towards the toy box. Then interest level estimation unit 60 estimates the level of interest based on the judged behavior of the target person and the aforementioned association. Note that the aforementioned association may be customized for a target person at home to which cleanup support system 1 is applied. For example, interest level estimation unit 60 included in cleanup support system 1 applied to a given home estimates, based on the association between the level of interest and the content of the behavior stored in storage unit 80 included in cleanup support system 1, that the level of interest is low when the movement of the target person at this given home is less than or equal to a fixed value. On the other hand, interest level estimation unit 60 included in cleanup support system 1 applied to another home may estimate, based on the association between the level of interest stored and the content of the behavior in storage unit 80 included in cleanup support system 1, that the level of interest is high when the movement of the target person at the another home is less than or equal to the fixed value. That is, interest level estimation unit 60 does not necessarily have to perform the estimation in the same manner for different homes. The difference is permitted because the content of the behavior estimated to draw a high (low) level of interest in the cleanup changes depending on, for example, the character of the target person.

Note that the level of interest is estimated, for example, in two steps including the level of interest which satisfies a predetermined criterion and the level of interest which does not satisfy the predetermined criterion. For example, it is estimated that the level of interest satisfies the predetermined criterion when the target person performs a behavior assumed to draw a high level of interest, while the level of interest does not satisfy the predetermined criterion when the target person performs a behavior assumed to draw a low level of interest. The predetermined criterion, for example, changes depending on a target person at home to which cleanup support system 1 is applied, and thus the predetermined criterion is defined for each target person. For a target person assumed to have a low level of interest when the movement is less than or equal to a fixed value, it is defined that the level of interest does not satisfy the predetermined criterion when the movement of the target person is, for example, less than or equal to 1 m.

Achievement level estimation unit 70 has the function of sequentially obtaining information indicating the weight of the toy box from weight meter 120 and estimating, based on the aforementioned information, the level of achievement of the cleanup performed by the target person. For example, achievement level estimation unit 70 judges whether or not the weight of the toy box has increased and thereby estimates the level of achievement. Note that the level of achievement is estimated, for example, in two steps including the level of achievement which satisfies a predetermined criterion and the level of achievement which does not satisfy the predetermined criterion. For example, when the weight of the toy box has increased by a fixed amount, it is estimated that the level of achievement satisfies the predetermined criterion and the cleanup behavior has been achieved, and when the weight of the toy box has not increased by the fixed amount, it is estimated that the level of achievement does not satisfy the predetermined criterion and the cleanup behavior has not been achieved. Note that, for example, the expression "the cleanup behavior has been achieved" does not mean that all the toys dispersed in the predetermined space have been stored into the toy box, but means that part of the aforementioned dispersed toys have been stored into the toy box, that is, the target person has performed the cleanup behavior.

First obtaining unit 10 obtains first information indicating the level of interest of the target person in the cleanup. Specifically, first obtaining unit 10 obtains the first information indicating the level of interest estimated by interest level estimation unit 60. More specifically, first obtaining unit 10 obtains, as the first information, information indicating whether or not the level of interest satisfies a predetermined criterion (whether or not the target person has interest the cleanup).

Second obtaining unit 20 obtains second information indicating the level of achievement of the cleanup performed by the target person. Specifically, second obtaining unit 20 obtains the second information indicating the level of achievement estimated by achievement level estimation unit 70. More specifically, second obtaining unit 20 obtains, as the second information, information indicating whether or not the level of achievement satisfies a predetermined criterion (whether or not the cleanup behavior has been achieved).

Determination unit 30 determines a content of control corresponding to the obtained first information and second information with reference to a rule which associates the level of interest in the cleanup and the level of achievement of the cleanup using the content of control performed on the device. Moreover, determination unit 30 determines the content of control without reference to the rule with a predetermined probability. Then determination unit 30 evaluates the behavior of the target person performed to control the device using the content of control determined without reference to the rule and, according to a result of the evaluation, and changes the probability of determining the content of control. More specifically, the result of the evaluation refers to the level of interest of the target person in the cleanup, and determination unit 30 changes the probability of determining the aforementioned content of control according to whether or not the level of interest with the content of control determined without reference to the rule satisfies the predetermined criterion. Moreover, the result of the evaluation may be the level of achievement of the cleanup performed by the target person and determination unit 30 may change the probability of determining the aforementioned content of control according to whether or not the level of achievement using the content of control determined without reference to the rule satisfies the predetermined criterion. The details of the operation of determination unit 30 will be described in (Operation) below.

Control unit 40 controls the device according to the determined content of control. The device is the one for supporting the cleanup behavior, and refers to, for example, any of display 130, projector 140, speaker 150, tablet 160, etc., described above. According to the determined content of control, control unit 40 controls display 130 to present a praise video or a cleanup-prompting video, controls projector 140 to project a cleanup-prompting moving image, controls speaker 150 to play praise music or cleanup-prompting music, and controls tablet 160 to provide a display prompting the target person to perform the cleanup by the caregiver.

Storage unit 80 stores rule 81 which associates the level of interest in the cleanup and the level of achievement of the cleanup using the content of control performed on the device. Specifically, storage unit 80 stores a plurality of rules 81 having mutually different contents of control performed on the device associated with the levels of interest in the cleanup and the levels of achievement of the cleanup. Note that storage unit 80 may be a storage unit different from a memory which stores control programs (computer programs) executed by the processor described above. Here, rules 81 will be described with reference to FIG. 3.

Figure 3:
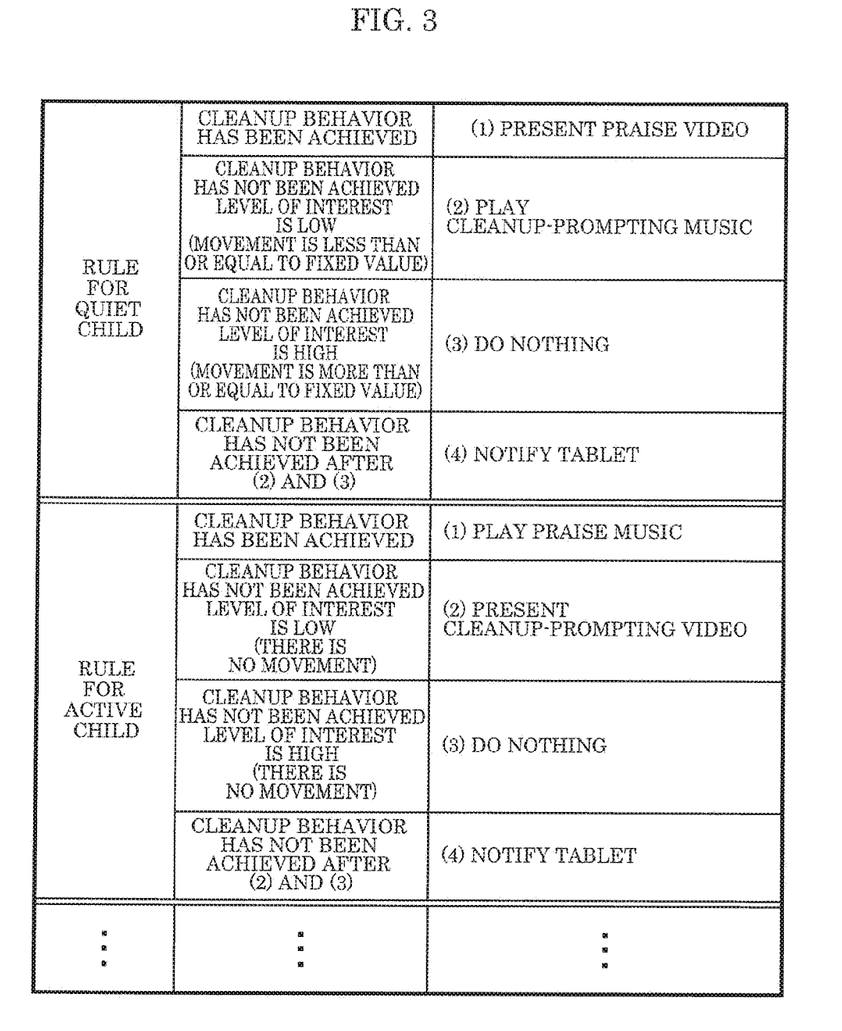
FIG. 3 is a diagram illustrating one example of rules.

FIG. 3 is a diagram illustrating one example of rules 81.

Rules 81 define the contents of control performed on the device according to the levels of achievement of the cleanup performed by the target person, more specifically, whether or not the level of achievement of the cleanup performed by the target person satisfies the predetermined criterion and according to the level of interest of the target person in the cleanup, more specifically, whether or not the level of interest of the target person in the cleanup satisfies the predetermined criterion. For example, according to the rule for a quiet child illustrated in FIG. 3, when the cleanup behavior has been achieved (when the level of achievement of the cleanup satisfies the predetermined criterion), (1) the video for praising the target person is presented from display 130. Moreover, in a case where the cleanup behavior has not been achieved, when the level of interest is low (when the level of interest does not satisfy the predetermined criterion), (2) the cleanup-prompting music is played from speaker 150. Moreover, in a case where the cleanup behavior has not been achieved, when the level of interest is high (when the level of interest satisfies the predetermined criterion), (3) no control is performed. Then in a case where the cleanup behavior has not been achieved even after above (2) or above (3), (4) tablet 160 is notified to cause the caregiver to prompt the target person to perform the cleanup. Moreover, for example, a voice supporting the target person or the like may be played instead of performing no control in above (3). Note that rule 81 may include the aforementioned association between the level of interest of the target person in the cleanup and the content of behavior that would be performed by the target person.

Depending on, for example, the attribute of the target person or an environment to which the target person belongs, a way in which the target person behaves may refer to a state in which the level of interest is high (or low), or the easiness for the target person to perform the cleanup behavior, etc., change depending on what content of control is used to control the device. Thus, storage unit 80 stores the plurality of rules 81. FIG. 3 illustrates, as one example of the plurality of rules 81, two rules (a rule for a quiet child and a rule for an active child) but the plurality of rules 81 may include two or more rules.

The plurality of rules 81 are respectively defined according to, for example, the attributes of the target person or the environments to which the target person belongs. The attributes of the target person mean the character, gender, age, etc., of the target person and the environments to which the target person belongs mean the size of a room where the target person plays, the number of siblings the target person has, etc.

For example, according to the rule for a quiet child, a state in which the movement of the target person is less than or equal to a fixed value indicates a low level of interest while according to the rule for an active child, a state in which there is no movement of the target person indicates a low level of interest, so that the content of behavior related to the level of interest changes depending on the type of the target person. The change occurs due to a difference in the content of the behavior estimated to draw a high (or low) level of interest in the cleanup depending on the character of the target person or the like, as described above. Moreover, for example, in a case where the cleanup behavior has not yet been achieved with a low level of interest, cleanup-prompting music is played according to the rule for a quiet child while the cleanup-prompting video is presented according to the rule for an active child, which means that the content of control performed on the device in order to prompt the cleanup changes between the two types of children. The change arises due to a difference in the content of control performed on the device which is likely to execute the cleanup behavior, depending on, for example, the character of the target person. As described above, the plurality of rules 81 are respectively defined according to, for example, the attributes of the target person or the environments to which the target person belongs.

Moreover, the plurality of rules 81 may include, for example, rules with mutually different reference values serving as the predetermined criterion employed upon determination that the level of interest is low (or high) although the contents of control performed when the level of interest is low (or high) are identical. That is, for example, it may be determined according to the given rule that the level of interest is low when the reference value as the movement is less than or equal to 1 m and it may be determined according to another rule that the level of interest is low when the reference value as the movement is less than or equal to 3 m. As described above, the plurality of rules 81 may include a strict rule according to which the level of interest is hardly determined to be high and a gentle rule according to which the level of interest is easily determined to be high.

Moreover, the plurality of rules 81 may similarly include, for example, rules with mutually different reference values for the predetermined criterion employed upon determination that the cleanup behavior has been achieved although the contents of control performed when the cleanup behavior has been achieved are identical. That is, for example, it may be determined according to a given rule that the cleanup behavior has been achieved when the weight of the toy box as the reference value has changed by 100 g or more for fixed time, and it may be determined according to another rule that the cleanup behavior has been achieved when the weight of the toy box as the reference value has changed by 200 g or more for the fixed time. As described above, the plurality of rules 81 may include a strict rule according to which it is hardly determined that the cleanup behavior has been achieved and a gentle rule according to which it is easily determined that the cleanup behavior has been achieved.

Selection unit 50 has the function of selecting one rule 81 from among the plurality of rules 81. Details of the operation of selection unit 50 will be described in [Operation] below.

[Operation]

Next, the operation of cleanup support system 1 will be described with reference to FIG. 4.

Figure 4:
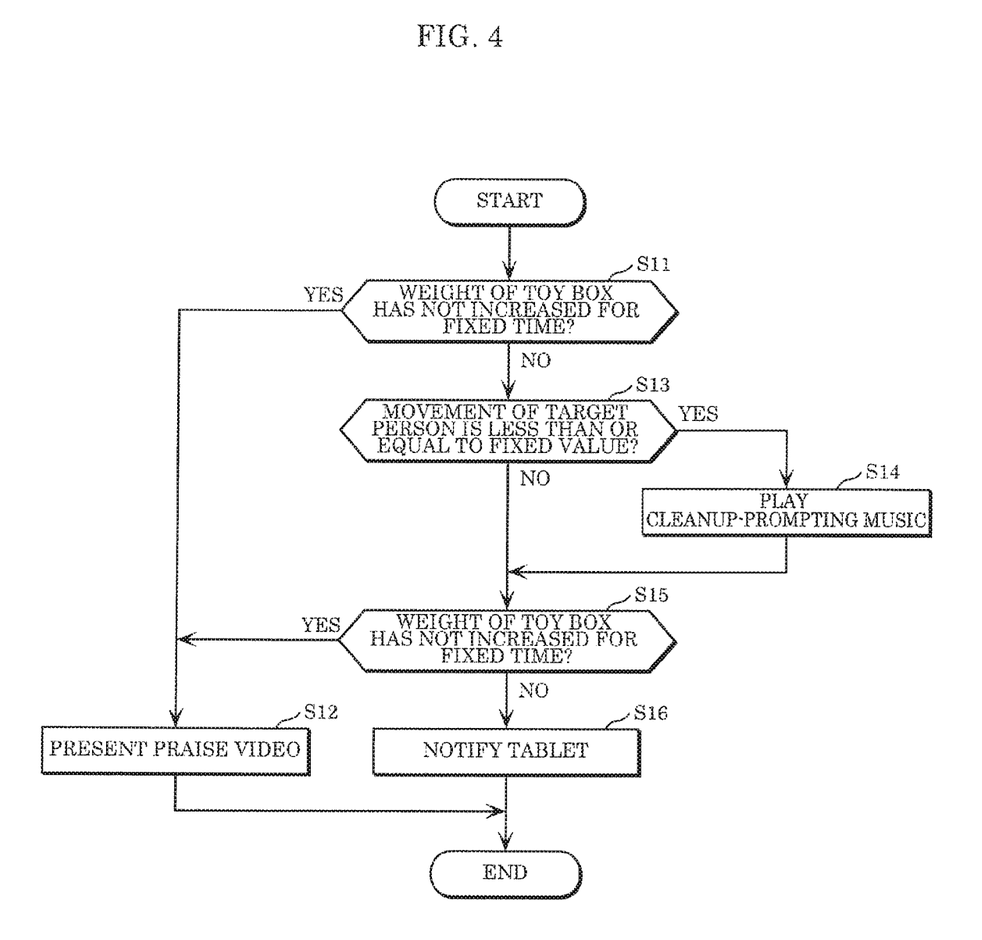
FIG. 4 is a flowchart illustrating one example of normal operation of the cleanup support system according to the embodiment.

FIG. 4 is a flowchart illustrating one example of normal operation of cleanup support system 1 according to the embodiment. FIG. 4 illustrates the operation of cleanup support system 1 according to the rule for a quiet child illustrated in FIG. 3.

First, determination unit 30 determines whether or not the weight of the toy box has increased for fixed time (step S11). That is, determination unit 30 determines whether or not the cleanup behavior has been achieved (whether or not the level of achievement of the cleanup satisfies the predetermined criterion). More specifically, determination unit 30 determines whether the second information obtained by second obtaining unit 20 is information indicating that the level of achievement of the cleanup satisfies the predetermined criterion or information indicating that the level of achievement does not satisfy the predetermined criterion.

Upon determination that the weight of the toy box has increased for the fixed time (Yes in step S11), determination unit 30 determines the content of control such that the praise video is presented (step S12). That is, with reference to rule 81 (for a quiet child), determination unit 30 determines the content of control (more specifically, the content of control (1) according to the rule for a quiet child in FIG. 3) corresponding to the second information indicating that the level of achievement of the cleanup satisfies the predetermined criterion (time cleanup behavior has been achieved). Consequently, control unit 40 causes display 130 to present the praise video.

Upon determination that the weight of the toy box has not increased for the fixed time (No in step S11), determination unit 30 determines whether or not the movement of the target person is less than or equal to a fixed value for the fixed time (step S13). That is, determination unit 30 determines whether or not the level of interest is low (whether or not the level of interest satisfies the predetermined criterion). More specifically, determination unit 30 determines whether the first information obtained by first obtaining unit 10 is information indicating that the level of interest in the cleanup does not satisfy the predetermined criterion or information indicating that the level of interest satisfies the predetermined criterion.

As described above, determination unit 30 determines the content of control according to whether or not the level of interest of the target person in the cleanup, which is indicated by the obtained first information, satisfies the predetermined criterion and whether or not the level of achievement of the cleanup performed by the target person, which is indicated by the obtained second information, satisfies the predetermined criterion.

Upon determination that the movement of the target person is less than or equal to the fixed value for the fixed three (Yes in step S13), determination unit 30 determines the content of control such that the cleanup-prompting music is played (step S14). Specifically, with reference to rule 81 (for a quiet child), determination unit 30 determines the content of control (more specifically, the content of control (2) according to the rule for a quiet child in FIG. 3) corresponding to the first information such that the level of interest in the cleanup does not satisfy the predetermined criterion. Consequently, control unit 40 causes speaker 150 to output the cleanup-prompting music.

Upon determination that the movement of the target person is not less than or equal to the fixed value for the fixed time (No in step S13), determination unit 30 determines a content of control such that nothing is performed for the fixed time. That is, with reference to rule 81 (rule for a quiet child), determination unit 30 determines the content of control (more specifically, the content of control (3) according to the rule for a quiet child in FIG. 3), corresponding to the first information, such that the level of interest in the cleanup satisfies the predetermined criterion. Therefore, in a case where the level of interest of the target person in the cleanup is high, cleanup prompting control is not performed in cleanup support system 1 even through the target person has not performed the cleanup behavior.

As described above, in a case where the level of achievement of the cleanup performed by the target person, which is indicated by the second information, does not satisfy the predetermined criterion, determination unit 30 determines that nothing is performed as the content of control performed on the device when the level of interest of the target person in the cleanup, which is indicated by the first information, satisfies the predetermined criterion. In a case where the aforementioned level of interest does not satisfy the predetermined criterion, determination unit 30 determines, as the content of control performed on the device, a content of control which prompts the target person to perform the cleanup.

Then determination unit 30 determines whether or not the weight of the toy box has not increased for the fixed time after step S13 or S14 (step S15). That is, determination unit 30 performs determination again whether or not the cleanup behavior has been achieved after the determination whether or not the level of interest is low.

Upon determination that the weight of the toy box has increased for the fixed time (Yes in step S15) determination unit 30 determines the content of control such that the praise video is presented (step S12).

On the other hand, upon determination that the weight of the toy box has not increased for the fixed time (No in step S15), determination unit 30 determines the content of control such that tablet 160 is notified (step S16). That is, with reference to rule 81 (for a quiet child), determination unit 30 determines, even after the determination of the content of control (2) or (3), the content of control corresponding to the second information indicating that the level of achievement of the cleanup does not satisfy the predetermined criterion (more specifically, the content of control (4) according to the rule for a quiet child in FIG. 3). Consequently, control unit 40 causes tablet 160 to provide, for example, a display indicating that the caregiver causes the target person to perform the cleanup, for example, the caregiver prompts the target person to perform the cleanup behavior by, for example, showing a model of cleanup to the target person by the caregiver.

The processing from steps S11 to S16 is repeatedly performed, for example, until dispersed toys are all stored into the toy box (the weight of the toy box measured with weight meter 120 reaches a specified value).

The operation of cleanup support system 1 according to one of rules 81 included in the plurality of rules 81 (for a quiet child) stored in storage unit 80 have been described above. One rule 81 described above is, for example, a rule selected by selection unit 50. Hereinafter, the way of selecting one rule 81 by selection unit 50 will be described.

Selection unit 50 selects one rule 81, for example, according to the operation performed on tablet 160 (operation unit). More specifically, the plurality of rules as illustrated in FIG. 3 are displayed on the display of tablet 160, so that the caregiver (the parent or the like) selects the rule assumed to agree with the character or the like of the target person (an infant or the like) from among the plurality of rules displayed (tablet 160 is operated). Then tablet 160 notifies the selected rule to cleanup support system 1 (selection unit 50) and selection unit 50 selects one rule corresponding to the notified rule. Note that the operation performed on tablet 160 may update (customize) rule 81 itself stored in storage unit 80 or may add a new rule. That is, the association between the level of interest and the content of behavior based on the given rule and the content of control performed on the device may be updated according to, for example, the attributes of the target person and the environments to which the target person belongs or a new rule may be created according to, for example, the attributes of the target person and the environments to which the target person belongs. Then selection unit 50 may select the new rule or the like as one rule 81.

Moreover, selection unit 50 selects one rule 81 according to, for example, the first information and second information obtained. For example, while the processing illustrated in steps S11 to S16 described above is repeatedly performed, in a case where the first information remains as the information indicating that the level of interest does not satisfy the predetermined criterion and the second information remains as the information indicating that the level of achievement does not satisfy the predetermined criterion, there is a risk that the currently selected rule is not suitable for the target person. For example, since the praise video is unsatisfactory (that is, unfavorite) as a reward obtained by achieving the cleanup behavior for the target person, the target person may assume that the reward obtained by achieving the cleanup behavior is small and thus may not perform the cleanup behavior whereby the level of achievement may not satisfy the predetermined criterion. Moreover, for example, the cleanup-prompting music does not produce in the target person motivation for the cleanup, and thus the level of interest of the target person in the cleanup may not increase even when the music is played whereby the level of interest may not satisfy the predetermined criterion.

Thus, in a case as described above, selection unit 50 selects the rule different from the rule currently selected. Consequently, it is possible that the content of control performed on the device is satisfactory as the reward obtained by achieving the cleanup behavior whereby the level of interest may increase. As described above, selection unit 50 may automatically determine one rule 81 according to the first information and second information obtained.

Moreover, selection unit 50 selects one rule 81, for example, according to a history of rules selected previously. For example, assume that a history such that the given specific rule has been selected on a specific day (for example, Sunday) previously is stored into storage unit 80 through operation performed by tablet 160. In this case, selection unit 50 automatically selects the aforementioned specific rule on specific days (for example, Sundays) thereafter according to the aforementioned history.

As described above, determination unit 30 determines the content of control corresponding to the first information and second information obtained with reference to rule 81, but determination unit 30 determines the content of control without reference to rule 81 with a predetermined probability. For example, when Yes is confirmed in step S13 while the processing from steps S11 to S16 is repeatedly performed, instead of performing the processing in step S14 (processing of determining the content of control with reference to rule 81), the content of control (for example, a content of control such that cleanup-prompting animation is presented) is determined without reference to rule 81 with the predetermined probability. The predetermined probability is not specifically limited and appropriately determined. For example, assume that the predetermined probability is 10%. Moreover, upon determining the content of control without reference to rule 81, determination unit 30 determines the content of control from among the plurality of contents of control. For example, assume that determination unit 30 determines the content of control from among the five contents of control without reference to rule 81. That is, when Yes is confirmed in step S13, instead of the processing of step S14, processing (that is, processing in step S21) of determining the content of control from among the five contents of control without reference to rule 81 with a probability of 10% is performed. The probability of determining each of the five contents of control upon the determination of the content of control without reference to rule 81 is uniform (20%).

Figure 5:
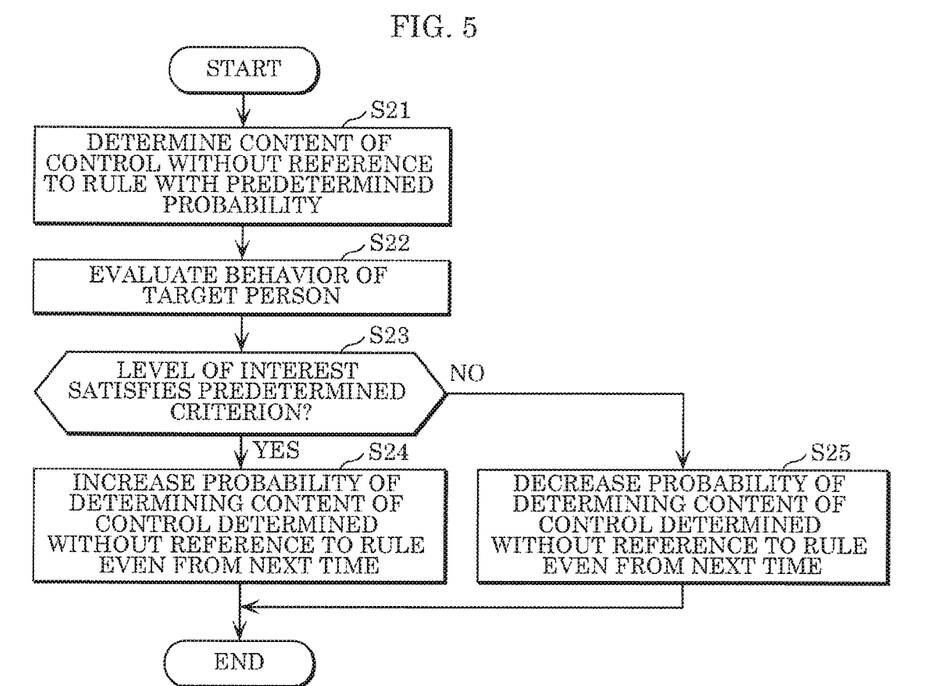
FIG. 5 is a flowchart illustrating one example of operation performed upon determining a content of control without reference to the rule by the cleanup support system according to the embodiment.

Hereinafter, operation of cleanup support system 1 performed upon determining the control content without reference to rule 81 will be described.

FIG. 5 is a flowchart illustrating one example of operation performed by cleanup support system 1 according to the embodiment upon determining the control content without reference to rule 81.

First, determination unit 30 determines the content of control without reference to rule 81 with the predetermined probability (step S21). For example, upon determination by determination unit 30 that the movement of the target person is less than or equal to the fixed value for the fixed time (Yes in step S13), processing in step S21 is performed. That is, the processing in step S14 is performed in normal cases, but the processing in step S21 is performed with the predetermined probability (probability of 10%).

Next, control unit 40 controls the device according to the content of control determined without reference to rule 81, and determination unit 30 evaluates the behavior of the target person performed to control the device based on the aforementioned content of control (step S22). The evaluation of the behavior of the target person is, for example, the evaluation of the level of interest of the target person in the cleanup, and. a result of evaluation is the aforementioned level of interest. That is, determination unit 30 performs the aforementioned evaluation based on the first information obtained by first obtaining unit 10 and the result of the evaluation is a result indicating whether or not the target person has interest in the cleanup.

Next, determination unit 30 determines whether or not the level of interest satisfies the predetermined criterion (step S23). More specifically, determination unit 30 determines whether or not the first information is information indicating that the level of interest satisfies the predetermined criterion.

Upon determination by determination unit 30 that the level of interest satisfies the predetermined criterion (Yes in step S23), that is, in a case where the target person has interest in the cleanup as a result of the control performed on the device using the content of control determined without reference to rule 81, the probability of determining the content of control determined without reference to rule 81 even from the next time is increased. (step S24). More specifically, upon determination of the content of control without reference to rule 81 next time by determination unit 30, the probability of determining, from among the plurality of contents of control, the content of control determined last time with the increased level of interest is increased. Referring to one example, assuming that determination unit 30 has determined the content of control from the five contents of control without reference to rule 81 with uniform probability (20%), the probability of determining the content of control determined last time with the increased level of interest of the target person from among the five contents of control upon determining the content of control without reference to rule 81 next time is increased to 30%, and the probability of determining the other four contents of control is decreased to 17.5%.

On the other hand, upon determination by determination unit 30 that the level of interest does not satisfy the predetermined criterion (No in step S23), that is, in a case where the target person does not have interest in the cleanup as a result of the control of the device using the content of control determined without reference to rule 81, the probability of determining the content of control determined without reference to rule 81 even from the next time is decreased (step S25). More specifically, upon determination of the content of control without reference to rule 81 next time by determination unit 30, the probability of determining, from among the plurality of contents of control, the content of control determined last time with the level of interest of the target person not increased is decreased. Referring to one example, assuming that determination unit 30 has determined the contents of control without reference to rule 81 with a uniform probability of 20% for the five content of controls, upon determination of the content of control without reference to rule 81 next time, the probability of determining, from among the five contents of control, the content of control determined last time with the level of interest of the target person not increased is decreased to 10%, and the probability of determining the other four contents of control is decreased to 22.5%.

Then out of the plurality of (for example, five) contents of control, the content of control that is likely to be determined is fixed as a result of repeatedly performing the processing from steps S11 to S16. Consequently, since it is recognized that the aforementioned content of control that is likely to be determined is a content of control with which the target person is likely to have interest in the cleanup, for example, in a case where the probability of determining the aforementioned content of control that is likely to be determined has increased to some extent, determination unit 30 updates rule 81 stored in storage unit 80. For example, determination unit 30 changes the content of control (2) according to the rule for a quiet child illustrated in FIG. 3 to the aforementioned content of control that is likely to be determined.

Note that the evaluation of the behavior of the target person in step S22 may be, for example, evaluation of the level of achievement of the cleanup performed by the target person. In this case, a result of the evaluation is the aforementioned. level of achievement. That is, determination unit 30 performs the evaluation based on the second information obtained by second obtaining unit 20 and the result of the evaluation serves as a result indicating whether or not the target person has achieved the cleanup. Then determination unit 30 determines in step S23 whether or not the level of achievement satisfies the predetermined criterion. More specifically, determination unit 30 determines whether or not the second information is information indicating that the level of achievement satisfies the predetermined criterion.

In this case, upon determination by determination unit 30 that the level of achievement satisfies the predetermined criterion, that is, in a case where the target person has performed the cleanup behavior through control of the device using the content of control determined without reference to rule 81, the probability of determining the content of control determined without reference to rule 81 even from the next time is increased. On the other hand, upon determination by determination unit 30 that the level of achievement does not satisfy the predetermined criterion, that is, in a case where the target person has not performed the cleanup behavior through the control of the device using the content of control determined. without reference to rule 81, the probability of determining the content of control determined without reference to rule 81 even from the next time is decreased.

SUMMARY

As described above, cleanup support system 1 according to the present embodiment is a system which supports a cleanup behavior. Cleanup support system 1 includes: first obtaining unit 10 which obtains first information indicating a level of interest of a target person in cleanup; and second obtaining unit 20 which obtains second information indicating a level of achievement of the cleanup performed by a target person. Cleanup support system 1 also includes: determination unit 30 which determines a content of control corresponding to the first information and second information obtained with reference to rule 81 which associates the level of interest in the cleanup and the level of achievement of the cleanup with the content of control performed on the device; and control unit 40 which controls the device according to the determined content of control. Then determination unit 30 determines the content of control without reference to rule 81 with a predetermined probability.

Typically, there is such a technology that performs, on a device, control of prompting the target person to perform cleanup if the target person has not achieved the cleanup behavior (if the target person has not performed the cleanup). However, in this case, the cleanup-prompting control may be performed regardless of the fact that the level of interest of the target person in the cleanup is high. In this case, the target person assumes that he or she is only required to perform the cleanup only when prompted to perform the cleanup, which reduces the level of interest in the cleanup, leading to the risk that the target person no longer spontaneously performs the cleanup. That is, there is a risk that the spontaneity of the target person is damaged in a case where the content of control is determined simply according to the level of achievement.

On the contrary, the content of control performed on the device is determined according to not only the level of achievement of the cleanup but also the level of interest in the cleanup in the present invention. For example, even in a case where the level of achievement of the cleanup is low (the cleanup behavior of the target person has not been achieved), when the level of interest in the cleanup is high, it is possible that the target person spontaneously performs the cleanup behavior, so that the target person can be watched for the fixed time without performing the cleanup-prompting control on the device. Moreover, for example, such control that supports the target person can be caused to be performed on the device to further increase the level of interest of the target person in the cleanup in this case. As described above, determining the content of control performed on the device according to not only the level of achievement but also the level of interest can increase the possibility that the target person more spontaneously performs the cleanup behavior.

Moreover, determination. unit 30 may further determine the content of control without reference to rule 81 with the predetermined probability.

Consequently, it is possible that the content of control which permits the target person to perform the cleanup more effectively than the content of control determined according to rule 81 is included in the contents of control determined without reference to rule 81, which can therefore increase the possibility that the target person can achieve the cleanup behavior.

Moreover, determination unit 30 may further evaluate the behavior of the target person performed to control the device using the content of control determined without reference to rule 81 and may change the probability of determining the aforementioned content of control according to a result of the evaluation. More specifically, the result of the evaluation refer to the level of interest of the target person in the cleanup, and determination unit 30 may change the probability of determining the aforementioned content of control according to whether or not the level of interest with the content of control determined without reference to rule 81 satisfies the predetermined criterion. Moreover, more specifically, the result of the evaluation refer to the level of achievement of the cleanup performed by the target person, and determination unit 30 may change the probability of determining the aforementioned content of control according to whether or not the level of achievement using the content of control determined without reference to rule 81 satisfies the predetermined criterion.

Consequently, in a case where the result of the evaluation is favorable, for example, the target person has achieved the cleanup behavior, for example, the probability of determining the aforementioned content of control can be increased, which can therefore more increase the possibility that the target person can achieve the cleanup behavior. More specifically, in a case where as the result of the evaluation, the level of interest or the level of achievement satisfies the predetermined criterion, for example, the probability of determining the aforementioned content of control can be increased, which can therefore more increase the possibility that the target person can achieve the cleanup behavior.

Moreover, determination unit 30 may determine the content of control according to whether or not the level of interest of the target person in the cleanup, which is indicated by the first information obtained, satisfies the predetermined criterion and according to whether or not the level of achievement of the cleanup performed by the target person, which is indicated by the second information obtained, satisfies the predetermined criterion.

Consequently, the determination of the level of interest and the level of achievement can be easily performed through two-step determination based on whether or not the predetermined criterion is satisfied.

Moreover, in a case where the level of achievement of the cleanup performed by the target person, which is indicated by the second information, does not satisfy the predetermined criterion, determination unit 30 may determine that nothing is performed as the content of control performed on the device when the level of interest of the target person in the cleanup, which is indicated by the first information, satisfies the predetermined criterion and may determine the content of control prompting the target person to perform the cleanup as the content of control performed on the device when the aforementioned level of interest does not satisfy the predetermined criterion.

Consequently, if the level of interest in the cleanup is high even when the target person has not performed the cleanup behavior, the target person can be watched for the fixed time without causing the cleanup-prompting control to be performed on the device, which can increase the possibility that the target person more spontaneously performs the cleanup behavior.

Moreover, cleanup support system 1 may further include selection unit 50 which selects one rule 81 from among the plurality of rules 81 indicating the mutually different contents of control performed on the device defined according to the level of interest in the cleanup and the level of achievement of the cleanup. Determination unit 30 may determine the content of control corresponding to the first information and second information obtained according to one rule 81 selected.

Consequently, the cleanup behavior performed by the target person can be supported by using the rule, out of the plurality of rules 81, which is suitable for the target person.

Moreover, cleanup support system 1 further includes an operation unit (tablet 160), and selection unit 50 may select one rule 81 according to operation performed on tablet 160.

Consequently, the caregiver or the like of the target person can select, from among the plurality of rules 81, the rule suitable for the target person by using the operation unit.

Moreover, selection unit 50 may select one rule 81 according to the first information and second information obtained.

Consequently, the rule suitable for the target person can be automatically selected according to the first information and the second information, that is, the current status of the target person.

Moreover, selection unit 50 may select one rule 81 according to a history of rules selected previously.

Consequently, the rule to be selected in the future can be adapted to have the same tendency as that of the rules selected previously. More specifically, in a case where the given specific rule was selected from tablet 160 or the like every Sunday previously, the aforementioned specific rule can be automatically selected on Sundays in future, which can omit the labor of manually selecting the aforementioned specific rule on Sundays.

Moreover, the plurality of rules 81 may be respectively defined according to the attributes of the target person.

Consequently, the rules suitable for the target person can be respectively selected from among the plurality of rules 81 according to the attributes (character, gender, age, etc.) of the target person.

Moreover, the plurality of rules 81 may be respectively defined according to the environments to which the target person belongs.

Consequently, the rules suitable for the target person can be respectively selected from among the plurality of rules 81 according to the environments (size of a room where the target person plays, the number of siblings the target person has, etc.) to which the target person belongs.

Other Embodiment

Cleanup support system 1 according to the embodiment has been described above, but the present invention is not limited to the embodiment described above.

For example, cleanup support system 1 includes interest level estimation unit 60 and achievement level estimation unit 70 in the embodiment described above, but cleanup support system 1 may not include interest level estimation unit 60 and achievement level estimation unit 70. For example, cleanup support system 1 may acquire the level of interest and the level of achievement estimated outside of the aforementioned system.

Moreover, for example, storage unit 80 stores the plurality of rules 81 in the embodiment described above, but storage unit 80 may store only one rule 81. In this case, cleanup support system 1 may not include selection unit 50.

Moreover, for example, achievement level estimation unit 70 in the present embodiment sequentially obtains information indicating the weight of the toy box from weight meter 120 and estimates the level of achievement of the cleanup performed by the target person based on the aforementioned information, but the present invention is not limited to this. For example, achievement level estimation unit 70 may, upon performance of the behavior by the target person, sequentially obtain, from camera 110, an image (image data) generated by photographing and may estimate the level of achievement of the cleanup performed by the target person based on this image. For example, achievement level estimation unit 70 may recognize, for example, by an image that the target person is going back and forth between the toy box and the toy to thereby estimate that the target person has achieved the cleanup behavior.

Moreover, determination unit 30 may change the aforementioned content of control little by little upon determining the content of control corresponding to the first information and second information obtained with reference to rule 81 which associates the level of interest in the cleanup and the level of achievement of the cleanup with the content of control performed on the device. For example, determination unit 30 changes, for example, the tempo of cleanup-prompting music little by little in step S14 illustrated in FIG. 4. Upon making the aforementioned change, determination unit 30 evaluates the behavior performed by the target person in the same manner as in step 22 illustrated in FIG. 5. For example, in a case where the result of the evaluation has improved as a result of slightly increasing the aforementioned tempo, determination unit 30 evaluates the behavior of the target person by further slightly increasing the tempo next time. Repeating this makes it possible to determine (learn) the optimum content of control (the tempo of the cleanup-prompting music here). As described above, determination unit 30 may perform reinforcement learning by slightly changing the content of control in order to determine the optimum content of control.

Moreover, even in a case where the level of interest of the target person in the cleanup, which is indicated by the first information obtained, satisfies the predetermined criterion, determination unit 30 may determine, with the predetermined probability, the same content of control as the content of control determined in a case where the level of interest does not satisfy the predetermined criterion. The aforementioned predetermined probability is not specifically limited and may be appropriately determined. More specifically, even in a case where the level of interest satisfies predetermined criterion in step S13 illustrated in FIG. 4 (No in step S13), the processing in step S14 is performed with the predetermined probability. Consequently, it is possible to more effectively perform the reinforcement learning.

Moreover, the present invention can be realized not only as cleanup support system 1 but also as a cleanup support method including a step (process) performed by each component forming cleanup support system 1.

Figure 6:
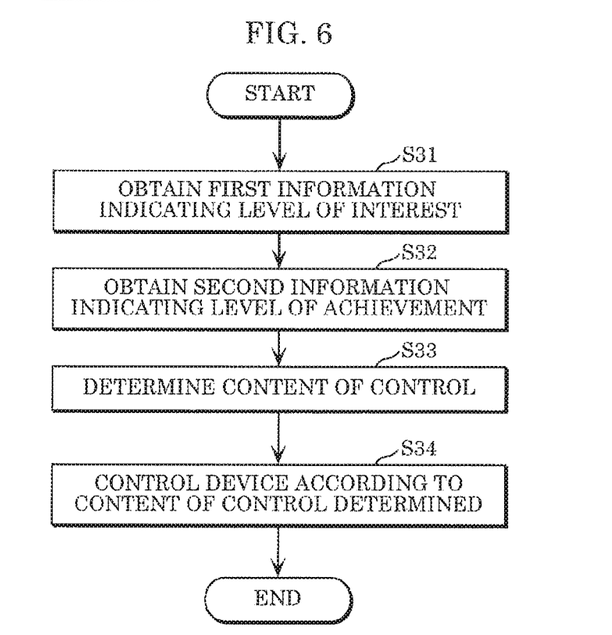
FIG. 6 is a flowchart illustrating one example of a cleanup support method.

FIG. 6 is a flowchart illustrating one example of the cleanup support method.

The cleanup support method is a method for supporting a cleanup behavior and includes: as illustrated in FIG. 6, obtaining (step S31) first information indicating the level of interest of the target person in the cleanup; obtaining (step S32) second information indicating the level of achievement of the cleanup performed by the target person; determining (step S33) a content of control corresponding to the first information and second information obtained with reference to rule 81 which associates the level of interest in the cleanup and the level of achievement of the cleanup with the content of control performed on the device; and controlling (step S34) the device according to the determined content of control.

For example, these steps may be executed by a computer (computer system). Then the present invention can be realized as a program (cleanup support program) for causing the computer to execute the steps included in these methods. Further, the present invention can be realized as a non-transitory, computer-readable recording medium such as a CD-ROM or the like on which the program is stored.

For example, in a case where the present invention is realized by a program (software), each of the steps is executed by execution of the program by use of hardware resources such as a CPU, a memory, an input and output circuit, etc. of the computer. That is, each of the steps is executed by obtaining, for example, from the input and output circuit or the memory, data by the CPU and performing calculation or outputting results of the calculation to, for example, the memory or the input and output circuit.

Moreover, each of the components included in cleanup support system 1 of the embodiment described above may be realized as a dedicated or general-purpose circuit.

Moreover, each of the components included in cleanup support system 1 of the embodiment described above may be realized as a large-scale integration (LSI) as an integrated circuit (IC).

Moreover, the integrated circuit is got limited to the LSI and may be realized by a dedicated circuit or general-purpose processor. A programmable field programmable gate array (FPGA) or a reconfigurable processor capable of reconfiguring connection and setting of a circuit cell inside of the LSI may be used.

Further, with the appearance of a technique of an integrated circuit replacing the LSI as a result of advancement of semiconductor technologies and another technique, it is needless to say that this technique may be used to provide an integrated circuit of each component included in cleanup support system 1.

In addition, the present invention also includes: a mode obtained by making various modifications conceivable by those skilled in the art to the embodiment; and a mode realized by combining components and functions in each embodiment in a desired manner within the scope not departing from the spirits of the present invention.

The invention claimed is:

1. A cleanup support system that supports a cleanup behavior, the cleanup support system comprising:
   a processor;
   a memory device storing a computer readable program code which when executed by the processor configures the processor to operate as, a first obtaining unit configured to obtain first information indicating a level of interest of a target person in cleanup;

a second obtaining unit configured to obtain second information indicating a level of achievement of the cleanup performed by the target person;

a determination unit configured to determine a content of control corresponding to the first information obtained and the second information obtained, with reference to a rule which associates the level of interest in the cleanup and the level of achievement of the cleanup with a content of control performed on a device; and a control unit configured to control the device according to the content of control determined, wherein the device is controlled such that the device generates an output which prompts the target person to perform cleanup, wherein the determination unit is further configured to determine the content of control without reference to the rule, with a predetermined probability, wherein the determination unit is configured to:

evaluate a behavior of the target person performed to control the device according to the content of control determined without reference to the rule; and changes the predetermined probability of determining the content of control according to an evaluation result.

2. The cleanup support system according to claim 1, wherein the evaluation result is the level of interest of the target person in the cleanup, and the determination unit is configured to change the predetermined probability of determining the content of control according to whether or not the level of interest with the content of control determined without reference to the rule satisfies a predetermined criterion.

3. The cleanup support system according to claim 1, wherein the evaluation result is the level of achievement of the cleanup performed by the target person, and the determination unit is configured to change the predetermined probability of determining the content of control according to whether or not the level of achievement using the content of control determined without reference to the rule satisfies a predetermined criterion.

4. The cleanup support system according to claim 1, wherein the determination unit is configured to determine the content of control according to whether or not the level of interest of the target person in the cleanup, which is indicated by the first information obtained, satisfies a predetermined criterion, and whether or not the level of achievement of the cleanup performed by the target person, which is indicated by the second information obtained, satisfies a predetermined criterion.

5. The cleanup support system according to claim 4, wherein in a case where the level of achievement of the cleanup performed by the target person, which is indicated by the second information, does not satisfy the predetermined criterion, the determination unit is configured to (i) determine to do nothing as the content of control performed on the device when the level of interest of the target person in the cleanup, which is indicated by the first information, satisfies the predetermined criterion, and (ii) determine a content of control which prompts the target person to perform the cleanup as the content of control performed on the device when the level of interest does not satisfy the predetermined criterion.

6. The cleanup support system according to claim 4, wherein even in a case where the level of interest of the target person in the cleanup, which is indicated by the first information obtained, satisfies the predetermined criterion, the determination unit is configured to determine, with a predetermined probability, a same content of control as the content of control performed when the level of interest does not satisfy the predetermined criterion.

7. The cleanup support system according to claim 1, wherein the processor is further configured to operate as:

a selection unit configured to select one rule from among a plurality of rules which associate mutually different contents of control performed on the device with the level of interest in the cleanup and the level of achievement of the cleanup, wherein the determination unit is configured to determine the content of control according to the first information obtained and the second information obtained with reference to the one rule selected.

8. The cleanup support system according to claim 7, further comprising:

an operation unit, wherein the selection unit is configured to select the one rule according to operation performed on the operation unit.

9. The cleanup support system according to claim 7, wherein the selection unit is configured to select the one rule according to the first information obtained and the second information obtained.

10. The cleanup support system according to claim 7, wherein the selection unit is configured to select the one rule according to a history of rules selected previously.

11. The cleanup support system according to claim 7, wherein the plurality of rules are respectively defined according to attributes of the target person.

12. The cleanup support system according to claim 7, wherein the plurality of rules are respectively defined according to environments to which the target person belongs.

13. A computer-implemented cleanup support method for supporting a cleanup behavior, the cleanup support method comprising:

obtaining first information indicating a level of interest of a target person in cleanup;

obtaining second information indicating a level of achievement of the cleanup performed by the target person;

determining a content of control corresponding to the first information obtained and the second information obtained, with reference to a rule which associates the level of interest in the cleanup and the level of achievement of the cleanup with a content of control performed on a device; and controlling, according to the content of control determined, the device to generate an output which prompts the target person to perform cleanup, wherein determining the content of control further includes determining the content of control without reference to the rule, with a predetermined probability, and wherein determining the content of control includes:

evaluating a behavior of the target person performed to control the device according to the content of control determined without reference to the rule; and changing the predetermined probability of determining the content of control according to an evaluation result.

14. A computer-readable, non-transitory recording medium having recorded thereon a cleanup support program that causes a computer to execute the cleanup support method according to claim 13.

* * * * *